(12) United States Patent
Marano-Ford

(10) Patent No.: US 6,869,418 B2
(45) Date of Patent: Mar. 22, 2005

(54) SAFETY SHIELD FOR A NEEDLE ASSEMBLY

(75) Inventor: April Marano-Ford, Manhattan Beach, CA (US)

(73) Assignee: Hypoguard USA Inc., Edina, MN (US)

( * ) Notice: Subject to any disclaimer, the term of this patent is extended or adjusted under 35 U.S.C. 154(b) by 285 days.

(21) Appl. No.: 09/932,830

(22) Filed: Aug. 17, 2001

(65) Prior Publication Data

US 2003/0036732 A1 Feb. 20, 2003

(51) Int. Cl.[7] .............................................. A61M 5/32
(52) U.S. Cl. ...................................................... 604/192
(58) Field of Search ................................ 604/111, 181, 604/187, 188, 192, 197, 198, 199, 263, 110

(56) References Cited

U.S. PATENT DOCUMENTS

| 4,664,259 | A | * | 5/1987 | Landis | 206/365 |
| 4,944,397 | A | * | 7/1990 | Miller | 206/365 |
| 5,152,751 | A | | 10/1992 | Kozlowski | 604/192 |
| 5,405,332 | A | | 4/1995 | Opalek | 604/192 |
| 5,599,313 | A | * | 2/1997 | Gyure et al. | 604/192 |

* cited by examiner

*Primary Examiner*—Manuel Mendez
(74) *Attorney, Agent, or Firm*—Fulbright & Jaworski L.L.P.

(57) ABSTRACT

A safety shield for a needle assembly which includes a cover, a mount and a hinge forming a shield body. The shield body defines a cavity in which a needle assembly having a needle and a luer hub is positioned. The mount includes a socket for receipt of the luer hub while the cover includes a retainer for coupling with the needle assembly. A hinge includes a living hinge between the cover and the mount. A tab encloses one end of the mount. Both the cover and the tab are associated with the mount by means of frangible webs to define a sealed body. A flexible tear strip extends over the cavity to fully seal the body.

43 Claims, 3 Drawing Sheets

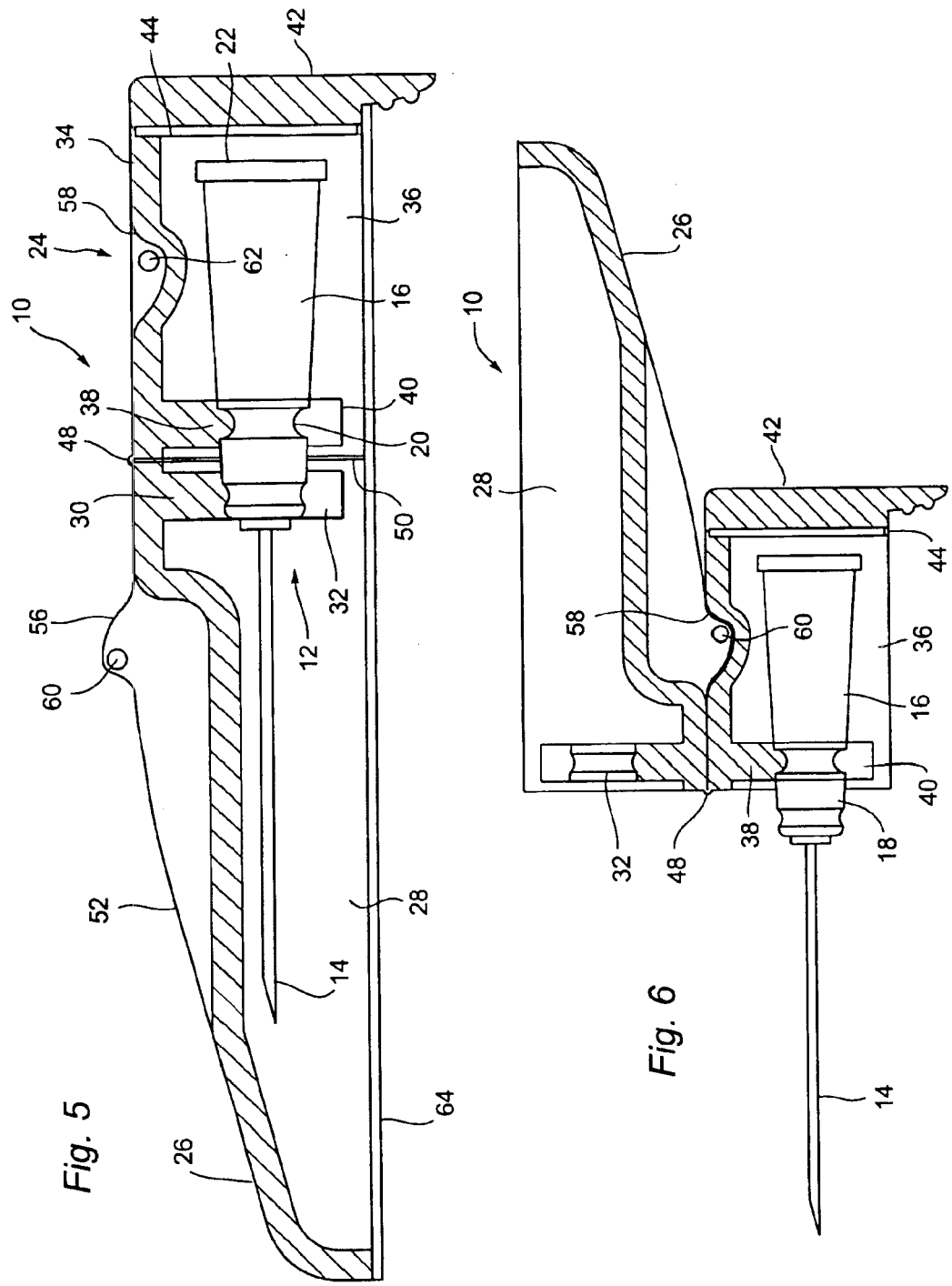

SAFETY SHIELD FOR A NEEDLE ASSEMBLY

BACKGROUND OF THE INVENTION

The field of the present invention is medical needle safety shields.

For some time, the art has recognized the desirability of protecting personnel from accidental sharps injuries or needle sticks. More recently, concerns have been expressed about the possibility of transmitting serious or potentially fatal infections as a result of such accidents. Most recently, legislation requiring the use of safe needle technology is pending in a number of States and before the Occupation Safety and Health Administration. Although, the art has recognized the desirability of protecting against accidental sharps injuries or needle sticks, truly practical, easily and safely manipulated and inexpensive protective devices are still not available. Accordingly, there is a need for a needle assembly having a safety mechanism to cover used needle points which is practical, easy to use and does not require elaborate manufacturing.

SUMMARY OF THE INVENTION

The present invention is directed to a safety shield for a needle assembly of the type having a needle and a luer hub. The safety shield includes a cover with an elongate channel that is retained over the needle, a mount having a socket to retain the luer hub and a hinge between the cover and the mount.

In a first separate aspect of the present invention, the safety shield further includes a flexible tear strip which extends over the channel to enclose the needle. Such a tear strip can be employed with the shield cover to define sterile packaging for the needle.

In a second separate aspect of the present invention, an end piece extends across an access end of the mount and provides a frangible sealing web between the mount and the end piece. Sealing and protection of the luer hub of the needle assembly may be accomplished by such an end piece.

In a third separate aspect of the present invention, a frangible locking web extends between the cover and the mount. The frangible locking hub provides a mechanism which may be used to lock the cover in place over the needle prior to use. A fracture of the web then allows the cover to be pivoted about the hinge to expose the needle for use.

In a fourth separate aspect of the present invention, the shield body defines an elongate open cavity. This cavity is provided by channels defined within the cover and the mount. A flexible tear strip extends over the cavity to enclose the needle. The configuration of the shield body provides for easy fabrication of the shield. Employment of the tear strip seals appropriate components of the needle assembly. The hinge may be a living hinge to further facilitate manufacture.

In a fifth separate aspect of the present invention, the safety shield is associated with the needle assembly with the cover further including a bevel to the closed end portion of the cover on the surface opposite the elongate channel, the needle being sharpened on a bevel facing the same direction as the cover bevel.

In a further separate aspect of the present invention, combinations of any of the foregoing aspects are contemplated.

Accordingly, it is an object of the present invention to provide an improved safety shield for needle assemblies. Other and further objects and advantages will appear hereinafter.

BRIEF DESCRIPTION OF THE DRAWINGS

FIG. 5 is a cross-sectional side view taken along line 5—5 of FIG. 2.

FIG. 6 is a cross-sectional side view as in FIG. 5 with the cover pivotally retracted.

DETAILED DESCRIPTION OF THE PREFERRED EMBODIMENT

Figure 1:
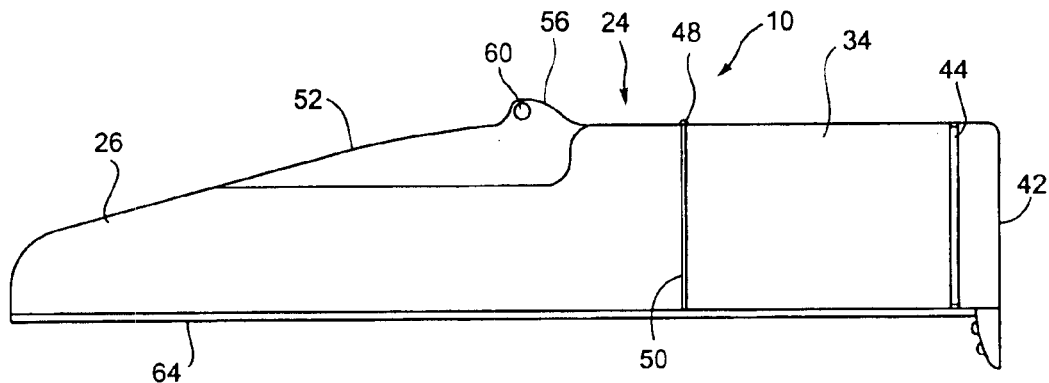
FIG. 1 is a side view of a safety shield.
Figure 2:
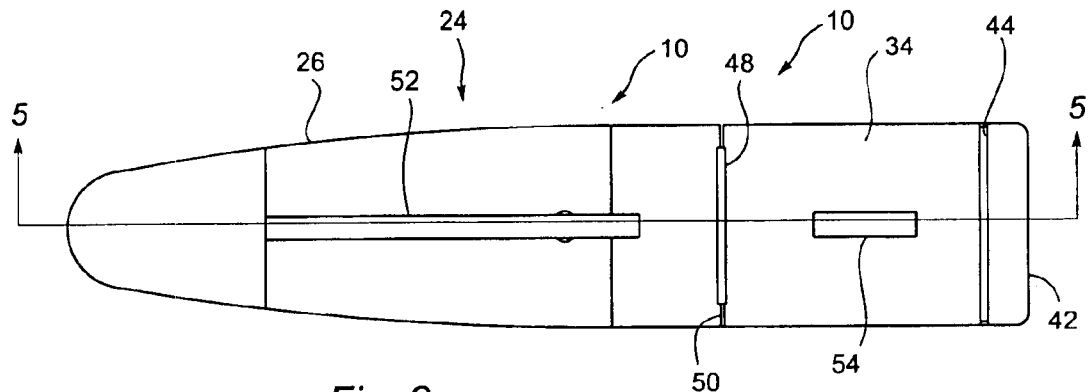
FIG. 2 is a plan view of the safety shield of FIG. 1.

Turning in detail to the figures, a safety shield 10 is associated with a needle assembly 12 including a needle 14 and a luer hub 16. The needle 14 is conventional as is the socket of the luer hub 16 to conform to standards. ISO-6009 color-coding is also used for the luer hub 16. The luer hub 16 further includes an anterior body 18 and a waist 20 between the anterior body 18 and the socket portion 22 of the luer hub 16.

The safety shield 10 includes a shield body, generally designated 24. The shield body 24 is a single piece molded product in the preferred embodiment, which may be medical grade or appropriate non-medical grade thermoplastic polymer or copolymer. Polystyrene or other appropriate easily molded or formed and easily sterilized material is contemplated. Even die cast or punched aluminum may be appropriate in certain circumstances.

The shield body 24 includes a cover 26 that has an elongate channel 28, which extends longitudinally of the shield body 24. The elongate channel 28 is closed at one end, generally U-shaped in lateral cross section along its length and has a generally flat peripheral edge generally lying in a plane and extending along both sidewalls as well as about the closed end portion. The upper surface of the cover 26 is sloped toward the closed end portion with a conveniently flat surface. The resulting bevel is generally parallel to the bevel on a needle positioned within as an indicator of the needle orientation. The bevel is also a convenient surface for indicia of needle specifications, such as gauge size, corresponding to the enclosed needle. Printing, embossing, color-coding in accordance with ISO-6009, and the like may be used.

The cover 26 further includes a retainer 30 within the elongate channel 28. In the preferred embodiment, the retainer 30 includes opposed flexible fingers 32 which are engaged with the anterior body 18 when the cover 26 is closed over the needle 14. A recess about the anterior body 18 receives the retainer 30. The fingers 32 may describe arcs of a circle to fit into the recess. The retainer 30 pivots from the recess off the end of the anterior body 18. The fingers 32 may alternatively be sized to engage the needle 14 rather than the anterior body 18. Further, the retainer may be an adhesive, a latch or other retaining mechanism and may actually provide a retaining force only after the cover 26 is opened and then returned to a position over the needle 14.

The shield body 24 also includes a mount 34. The mount 34 is formed with a channel 36 aligned with the open cavity of the shield body 24. Together, the cover 26 and the mount 34 define an elongate open cavity of the shield body 24. The mount 34 includes a socket 38 for rigidly retaining the needle assembly 12. The socket 38 also includes opposed fingers 40 which extend about the waist 20 of the luer hub 16 and configured to grip the waist 20 more tenaciously than the retainer 30 grips the recess.

The mount 34 has an access end which is closed by an end piece 42. The end piece 42 extends across the access end of the mount 34 and is fixed thereto by a frangible sealing web 44 which extends about the end of the mount 34 where the channel 36 intersects the end piece 42 in a U-shaped configuration. The end piece 42 includes a finger tab 46 for gripping the end piece 42 to tear the sealing web 44 and fully remove the end piece 42. Through the removal of the end piece 42, access is provided through the access end of the mount 34 to the socket of the luer hub 16.

A hinge 48 is positioned to mount the cover 26 to the mount 34. The hinge 48 is a living hinge integrally molded with the remainder of the shield body 24. The hinge 48 extends for a short distance across the top of the shield body 24 in order that the cover 26 may be pivoted to a position as illustrated in FIG. 6.

Figure 3:
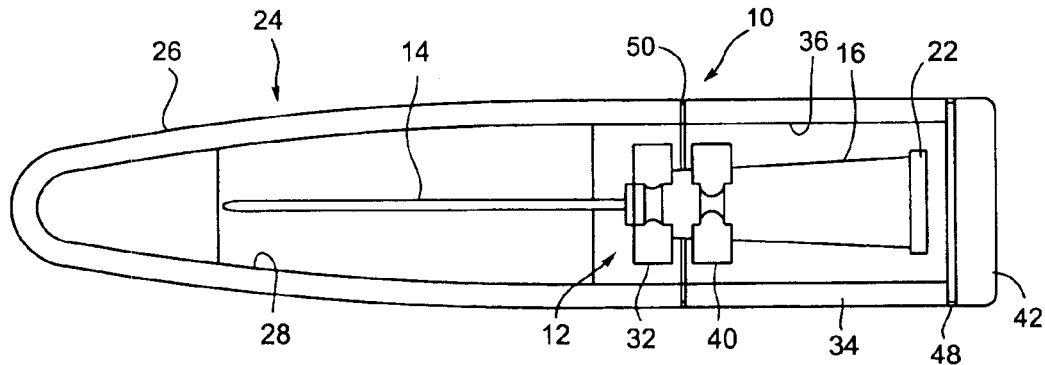
FIG. 3 is a bottom view of the safety shield of FIG. 1.
Figure 4:
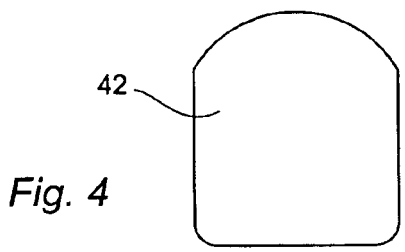
FIG. 4 is an end view of the safety shield of FIG. 1.

The remainder of the part line between the cover 26 and the mount 34 is closed and connected by a frangible locking web 50. This locking web 50 extends from either side of the hinge 48 about the full intersection between the cover 26 and the mount 34. Thus, the hinge 48 and the frangible locking web 50 define a U-shaped structure, unbroken for sealing purposes, or continuously impervious, to the flat peripheral edge. The sides of the cover 26 are deformable inwardly to fracture the frangible locking web 50. Once fractured, the cover 26 can be rotated from over the needle 14 about the living hinge 48. As can be seen in FIG. 3, the fingers 32 of the retainer are displaced inwardly from the sides of the channel 26 in order that the channel may be deformed inwardly for fracture of the locking web 50. The fingers 40 of the socket 38 may be as shown if the frangible locking web 50 is sufficiently weak that squeezing of the cover 26 without squeezing the sides of the mount 34 will fracture the locking web 50. The fingers 40 of the socket 38 may actually extend out to support the sides of the mount 34 to insure that the locking web 50 will be broken on each side.

An engagement is associated with the cover 26 and the mount 34. The engagement includes an element 52 on the cover 26 and an element 54 on the mount 34. The engagement of the elements 52 and 54 is engageable with the cover 26 rotated about the living hinge 48 into juxtaposition with the mount 34 as illustrated in FIG. 6. The elements 52 and 54 may be positioned as shown in the preferred embodiment or reversed. The element 52 is shown to include a tab 56 while the element 54 includes a socket 58. The tab 56 and the socket 58 are engageable with interference by means of a protrusion 60 on the tab 56 and a recess 62 on the socket 58. The protrusion 60 and recess 62 extend perpendicular to the elongate cavity and, when engaged, hold the cover 26 away from the needle 14 as shown in FIG. 6.

The safety shield further includes a flexible tear strip 64. The flexible tear strip 64 extends over the open cavity from the closed end portion of the cover 26 to the end piece 42. It is sealed to the edges of the channels defining the cover 26 and the mount 34, including about the closed end portion of the covet 26 and across the end piece 42 closing the access of the mount 34. The flexible tear strip 64 also seals to the ends of the locking web 50 and to the ends of the sealing web 44. This sealing is all accomplished with the cover 26 extending over the needle 14 to seal the entire interior of the elongate cavity of the shield body 24. The flexible tear strip 64 may include a tab extending beyond the periphery of the shield body 24 for easy purchase. The strip 64 may be of paper or plasticized paper, plastic, aluminum foil or other appropriate material.

In operation, the shield body 24 is molded as one piece in the preferred embodiment. The frangible locking web 50, in cooperation with the living hinge 48, and the frangible sealing web 44 seal between the mount 34, the cover 26 and the end piece 42 to create a cavity with no interstices but through the open side of the channels 28, 36. The needle assembly is then positioned within this structure with the waist 20 of the luer body 16 press fit into the socket 38. The anterior body 18 is also pressed into between the fingers 32 of the retainer 30. The planar edge surface about the channels 28, 36 and across the end piece 42 receives the flexible tear strip, attached by adhesive, thermal welding or chemical bonding or the like. With the placement of the tear strips 64, the needle assembly 12 is fully sealed within the shield body 24. Conventional sterilization may occur, if not already performed, through gamma radiation, electron beam radiation, ethylene oxide or the like.

Figure 7:
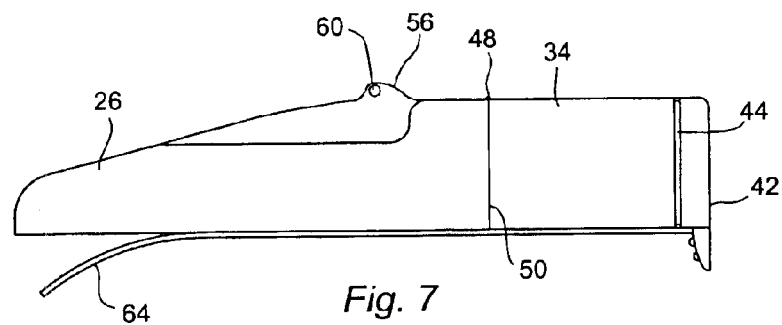
FIG. 7 is a side view of the safety shield of FIG. 1 with a flexible tear strip partially removed.
Figure 8:
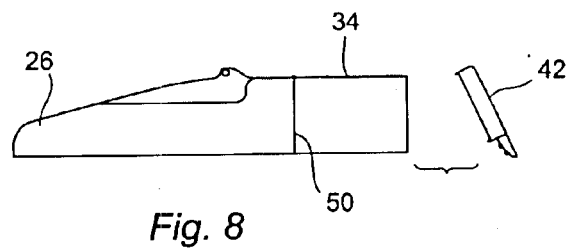
FIG. 8 is a side view of the safety shield of FIG. 1 with the flexible tear strip removed and an end piece broken from the end of the shield.
Figure 9:
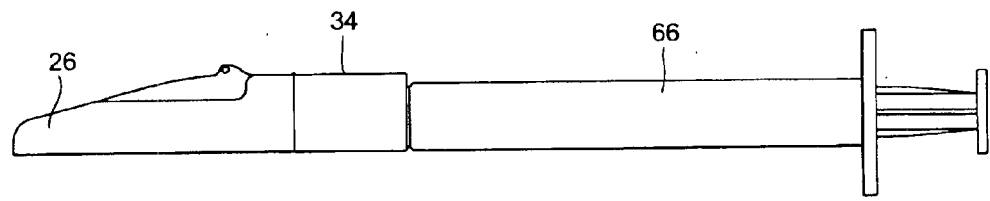
FIG. 9 is a side view of a safety shield assembled with a syringe.
Figure 10:
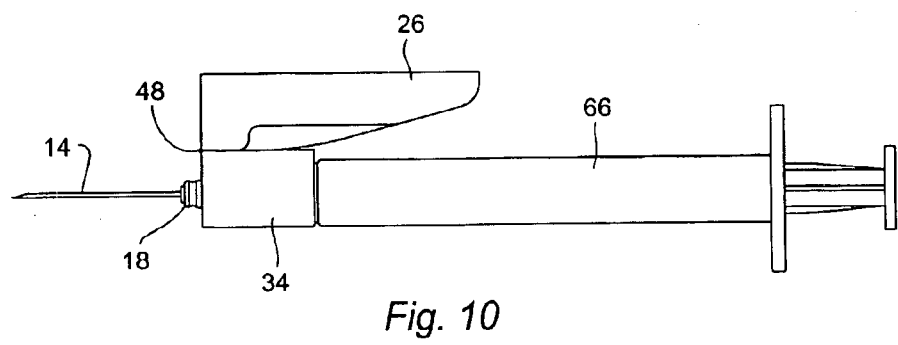
FIG. 10 is a side view of a safety shield assembled with a syringe with a cover pivotally mounted from over the needle.

In use, the shield body 24 is gripped with access to the flexible tear strip 64. The flexible tear strip 64 is removed as illustrated in FIG. 7. Next, the end piece 42 is removed as illustrated in FIG. 8. At this point, the socket of the luer hub is exposed and a syringe body 66, catheter or other device cooperating with a luer hub can be attached thereto as illustrated in FIG. 9. The sides of the cover 26 are then pinched to fracture the frangible locking hub 50. The cover 26 is then rotated about the living hinge 48 to engage the tab 56 with the socket 58. The assembly is then ready for a sterile hypodermic procedure. Once the procedure is complete, the tab 56 and socket 58 are forced apart and the cover 26 is once again positioned over the needle 14. The cover 26 is forced such that the fingers 32 of the retainer 30 engage the anterior body 18. The syringe body 66 may be disassembled from the safety shield 10 if desired or left in place with the safety shield 10 being disposed.

Accordingly, an improved safety shield is disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A safety shield for a needle assembly with a needle and a luer hub, comprising
   a cover including an elongate channel and a retainer engageable with the needle assembly with the elongate channel positioned over the needle;
   a mount including a socket to rigidly retain the luer hub of the needle assembly;
   a hinge, the cover being mounted to the mount by the hinge with the elongate channel extending longitudinally from the hinge;
   a flexible tear strip extending over the channel, enclosing the needle within the channel.

2. The safety shield of claim 1, the mount further having an access end providing access to the end of the luer hub.

3. The safety shield of claim 2 further comprising
   an end piece extending across the access end and a frangible sealing web between the mount and the end piece.

4. The safety shield of claim 1 further comprising
a frangible locking web extending between the cover and the mount.

5. The safety shield of claim 4, the cover having at least a first side deformable inwardly to fracture the frangible locking web between the cover and the mount.

6. The safety shield of claim 1, the retainer being within the channel.

7. The safety shield of claim 6, the retainer having a finger fixed to the cover and engageable with the needle assembly.

8. The safety shield of claim 6, the retainer having opposed fingers fixed to the cover and engageable with the needle assembly.

9. A safety shield for a needle assembly with a needle and a luer hub, comprising
a cover including an elongate channel and a retainer engageable with the needle assembly with the elongate channel positioned over the needle;
a mount including a socket to rigidly retain the luer hub of the needle assembly and an access end providing access to the end of the luer hub;
a hinge, the cover being mounted to the mount by the hinge with the elongate channel extending longitudinally from the hinge;
an end piece extending across the access end;
a frangible sealing web between the mount and the end piece.

10. A safety shield for a needle assembly with a needle and a luer hub, comprising
a needle cover including an elongate first channel;
a mount retaining the luer hub including a second channel aligned with the elongate first channel;
a hinge pivotally coupling the needle cover and the mount between the needle cover and the mount;
a frangible locking web extending between the cover and the mount from both sides of the hinge to the edges of the first and second channels, the hinge and the frangible locking web being continuously impervious between the cover and the mount.

11. The safety shield of claim 10 further comprising
a flexible tear strip affixed to the edges of the elongate first channel and the second channel and to the frangible locking web at the edges of the elongate first channel and the second channel, enclosing the needle within the elongate first channel.

12. A safety shield for a needle assembly with a needle and a luer hub, comprising
a cover including an elongate channel and a retainer engageable with the needle assembly with the elongate channel positioned over the needle;
a mount including a socket to rigidly retain the luer hub of the needle assembly;
a hinge, the cover being mounted to the mount by the hinge with the elongate channel extending longitudinally from the hinge;
a frangible locking web extending between the cover and the mount.

13. The safety shield of claim 12, the channel having at least a first side deformable inwardly to fracture the frangible locking web between the cover and the mount.

14. The safety shield of claim 12, the hinge being a living hinge.

15. The safety shield of claim 12 further comprising
an engagement including a first element on the cover and a second element on the mount, the first and second elements being engageable with the cover pivoted to lie in juxtaposition with the mount.

16. A safety shield for a needle assembly with a needle and a luer hub, comprising
a shield body generally forming an elongate open cavity and including a cover, a mount and a hinge, the cover being mounted to the mount by the hinge and having an elongate first channel extending longitudinally from the hinge and a retainer engageable with the needle assembly with the elongate first channel positioned over the needle, the mount having a second channel with a socket therein to rigidly retain the luer hub of the needle assembly;
a flexible tear strip extending over the cavity, closing the first and second channels and enclosing the needle within the cover with the luer hub in the socket.

17. The safety shield of claim 16, the mount further including an access end providing access to the end of the luer hub.

18. The safety shield of claim 17, the shield body further including an end piece extending across the access end of the mount and a frangible web between the mount and the end piece, the flexible tear strip extending to the end piece and sealing the elongate cavity along with the end piece.

19. The safety shield of claim 16 the shield body further including a frangible locking web extending between the cover and the mount and from the hinge on both sides to the flexible tear strip.

20. The safety shield of claim 19, the channel having at least a first side deformable inwardly to fracture the frangible locking web between the cover and the mount.

21. The safety shield of claim 19, the hinge being a living hinge.

22. A safety shield for a needle assembly with a needle and a luer hub, comprising
a shield body generally forming an elongate open cavity and including a cover, a mount, a hinge and an end piece, the cover being mounted to the mount by the hinge and having an elongate first channel extending longitudinally from the hinge and a retainer engageable with the needle assembly with the elongate first channel positioned over the needle, the mount having a second channel with a socket therein to rigidly retain the luer hub of the needle assembly and an access end providing access to the end of the luer hub, the end piece extending across the access end of the mount and a frangible sealing web between the mount and the end piece;
a flexible tear strip extending over the open cavity, closing the first and second channels and enclosing the needle within the cover with the luer hub in the socket, the flexible tear strip extending to the end piece and sealing the open cavity along with the end piece.

23. The safety shield of claim 22 the shield body further including a frangible locking web extending between the cover and the mount and from the hinge on both sides to the flexible tear strip.

24. The safety shield of claim 23, the cover having at least a first side deformable inwardly to fracture the frangible locking web between the cover and the mount.

25. The safety shield of claim 23, the hinge being a living hinge.

26. A safety shield and needle assembly comprising
a needle;
a luer hub, the needle extending from the luer hub;
a cover including an elongate channel with a closed end portion and a retainer engageable with the needle with the elongate channel positioned over the needle;

a mount including a socket to rigidly retain the luer;

a hinge, the cover being mounted to the mount by the hinge with the elongate channel extending longitudinally from the hinge;

a flexible tear strip extending over the channel, enclosing the needle within the channel.

27. The safety shield and needle assembly of claim 26, the cover further including a bevel to the closed end portion on the surface opposite the elongate channel, the needle being sharpened on a bevel facing the same direction as the cover bevel.

28. The safety shield and needle assembly of claim 26, the mount further having an access end providing access to the end of the luer hub.

29. The safety shield and needle assembly of claim 28 further comprising an end piece extending across the access end and a frangible sealing web between the mount and the end piece.

30. The safety shield and needle assembly of claim 26 further comprising a frangible locking web extending between the cover and the mount.

31. A safety shield and needle assembly comprising a needle;

a luer hub, the needle extending from the luer hub;

a cover including an elongate channel with a closed end portion and a retainer engageable with the needle with the elongate channel positioned over the needle;

a mount including a socket to rigidly retain the luer;

a hinge, the cover being mounted to the mount by the hinge with the elongate channel extending longitudinally from the hinge;

a frangible locking web extending between the cover and the mount.

32. The safety shield and needle assembly of claim 31, the cover further including a bevel to the closed end portion on the surface opposite the elongate channel, the needle being sharpened on a bevel facing the same direction as the cover bevel.

33. The safety shield and needle assembly of claim 31, the mount further having an access end providing access to the end of the luer hub.

34. The safety shield and needle assembly of claim 33 further comprising an end piece extending across the access end and a frangible sealing web between the mount and the end piece.

35. The safety shield and needle assembly of claim 31 further comprising a frangible locking web extending between the cover and the mount.

36. A safety shield and needle assembly comprising a needle;

a luer hub, the needle extending from the luer hub;

a shield body generally forming an elongate open cavity and including a cover, a mount, a hinge and an end piece, the cover being mounted to the mount by the hinge and having an elongate first channel extending longitudinally from the hinge and a retainer engageable with the needle assembly with the elongate first channel positioned over the needle, the mount having a second channel with a socket therein to rigidly retain the luer hub of the needle assembly and an access end providing access to the end of the luer hub, the end piece extending across the access end of the mount and a frangible sealing web between the mount and the end piece;

a flexible tear strip extending over the open cavity, closing the first and second channels and enclosing the needle within the cover with the luer hub in the socket, the flexible tear strip extending to the end piece and sealing the open cavity along with the end piece.

37. The safety shield and needle assembly of claim 36, the cover further including a bevel to the closed end portion on the surface opposite the elongate channel, the needle being sharpened on a bevel facing the same direction as the cover bevel.

38. The safety shield and needle assembly of claim 36 the shield body further including a frangible locking web extending between the cover and the mount and from the hinge.

39. The safety shield and needle assembly of claim 38, the cover having at least a first side deformable inwardly to fracture the frangible locking web between the cover and the mount.

40. The safety shield and needle assembly of claim 38, the hinge being a living hinge.

41. A safety shield for a needle assembly with a needle and a luer hub, comprising a needle cover including an elongate first channel;

a mount retaining the luer hub including a second channel aligned with the elongate first channel and having an access end;

a hinge pivotally coupling the needle cover and the mount between the needle cover and the mount;

a frangible locking web extending between the cover and the mount from both sides of the hinge to the edges of the first and second channels, the hinge and the frangible locking web being continuously impervious between the cover and the mount;

an end piece extending across the access end;

a frangible sealing web between the mount and the end piece;

a flexible tear strip affixed to the edges of the elongate first channel, the edges of the second channel and the end piece, enclosing the needle assembly within the needle cover and mount.

42. The safety shield for a needle assembly of claim 41, the hinge being a living hinge.

43. The safety shield of claim 10, the hinge being a living hinge.

* * * * *